United States Patent [19]

Lemke

[11] Patent Number: 5,419,313

[45] Date of Patent: May 30, 1995

[54] MICROWAVE STERILIZABLE AND REUSABLE ENDOSCOPE

[75] Inventor: Norbert Lemke, Veilchenstrasse 10, D-8031 Puchheim, Germany

[73] Assignees: Rosemarie Lemke; Norbert Lemke, both of Germany

[21] Appl. No.: 203,485

[22] Filed: Feb. 28, 1994

Related U.S. Application Data

[63] Continuation of Ser. No. 46,904, Apr. 14, 1993, abandoned, which is a continuation of Ser. No. 912,671, Jul. 14, 1992, abandoned, which is a continuation of Ser. No. 477,937, Jun. 27, 1990, abandoned.

[30] Foreign Application Priority Data

Oct. 27, 1988 [DE] Germany .................. 38 36 649.5
Apr. 18, 1989 [DE] Germany .................. 39 12 720.6

[51] Int. Cl.⁶ .............................................. A61B 1/06
[52] U.S. Cl. ................................................... 128/6
[58] Field of Search .................. 128/6, 11, 13, 16, 18; 604/20-21; 606/15-17

[56] References Cited

U.S. PATENT DOCUMENTS

| | | | |
|---|---|---|---|
| 2,843,112 | 7/1958 | Miller | 128/6 |
| 3,132,646 | 5/1964 | Heit | 128/6 |
| 4,323,304 | 4/1982 | Ishii | 128/6 |
| 4,475,539 | 10/1984 | Konomura | 128/6 |
| 4,475,540 | 10/1984 | Takamatsu | 128/6 |
| 4,586,491 | 5/1986 | Carpenter | 128/6 |
| 4,704,007 | 11/1987 | Landre et al. | 128/6 |
| 4,784,144 | 11/1988 | Ono et al. | 128/6 |
| 4,790,295 | 12/1988 | Tashiro | 128/6 |
| 4,914,521 | 4/1990 | Adair | 128/6 |
| 4,921,326 | 5/1990 | Wild et al. | 128/6 |

*Primary Examiner*—William E. Kamm
*Attorney, Agent, or Firm*—Evenson, McKeown, Edwards & Lenahan

[57] ABSTRACT

An endoscope has an objective arranged at its distal end, the image of which a relay-lens system conveys to the proximal end of the endoscope a light guide at least partially surrounds the relay-lens system and the objective, and conveys illumination light of an illumination light source from a light-entry connection to the distal end.

The light guide is provided with a hollow-cylinder made of a transparent and optically clear material which surrounds the objective and the relay-lens system. The light from the illumination light source can be coupled into the circular front face of the hollow cylinder.

7 Claims, 2 Drawing Sheets

MICROWAVE STERILIZABLE AND REUSABLE ENDOSCOPE

This application is a continuation of application Ser. No. 08/046,904, filed Apr. 14, 1993, now abandoned, which is a continuation of application Ser. No. 07/912,671, filed Jul. 14, 1992, now abandoned, which is a continuation of application Ser. No. 07/477,937, filed Jun. 27, 1990, now abandoned.

BACKGROUND AND SUMMARY OF THE INVENTION

The present invention relates to an endoscope having arranged at to distal end an endoscope objective whose image is conveyed by an image-carrying unit to a proximal end. A TV camera can be attached to the proximal end of the endoscope to pick up the image. The endoscope has an illumination device, which is provided with a light guide to convey light from a light source to the distal end and which encompasses the image-carrying unit. The present invention also relates to a method for sterilizing the aforementioned endoscope.

Endoscopes are presently employed in medicine and technology in a great variety of applications. The standard endoscopes offered have arranged at the distal end thereof a endocope lens, the image of which an image-carrying unit conveys to the proximal end, where an operator can observe it by means of an eyepiece or a TV camera which is usually mounted on the eyepiece. An illumination device is usually provided with a light guide to convey the light from the light source to the distal end and encompasses the image-guiding unit.

In order to couple-in the illumination light required for illuminating the cavity in which the endoscope is utilized, the prior art endoscopes have a lateral, largely standard light-line connection socket which can be connected to a light-guide cord of an illumination light source. Leading out of this lateral illumination light-guide connection socket to the distal end are a large number of light-guide fibers which are laid in the cavity between the relay-lens system and an outer protective metal tube.

The fabrication of the conventional light guide composed of a large number of light-guide fibers is too complicated for several reasons:

First, the light-guide fibers have to be "prearranged by hand" when assembling the endoscope.

Second, the individual light-guide fibers have to be ground and bent in compliance with the angle of vision of the lens situated at the distal end in order for the axis of the illumination to some extent conform with the optical axis of the lens.

Third, the prior art endoscopes have the disadvantage that the light-guide fibers and, under certain circumstances, also the cemented sections in the endoscope makes autoclave sterilization feasible only to a limited extent. "In solution" sterilization is, however, inadequate in particular in view of diseases such as AIDS, etc.

If instead of, or in addition to, normal direct observation of the endoscope image, representation of this image on a monitor is desired, presently a miniature TV camera that picks up the "eyepiece image" in the conventional manner with a lens and an image pick-up is either attached directly to a concha shaped eyepiece or via an image divider.

These prior art endoscopes are shown in DE 37 43 920 A1 and have a number of disadvantages First of all, the miniature TV camera is still relatively large due to the required size lens, the image pick-up, etc. Usually the camera is from 8 to 10 cm long and has a cross-section of several centimeters.

Second, the TV camera extends the length of the endoscope, thereby altering, the weight distribution detrimentally affecting the handling of the unit as a whole.

Third, the optics of the TV camera are relatively elaborate as an image of an eyepiece has to be represented.

An object of the present invention is to improve an endoscope having an endoscope lens arranged at the distal end thereof, the image of which is conveyed by an image-carrier unit to the proximal end to which a TV camera can be attached for picking up the image. An illumination device is provided with a light guide and conveys the light from a light source to the distal end. The illumination device encompasses the image-carrying unit in such a manner that video-image representation is possible with simple means and simple construction.

Moreover, an endoscope having a lens arranged at the distal end thereof, the image of which is conveyed by a relay-lens system to the proximal end, and having a light guide which at least partially surrounds the relay-lens system and the lens and which conveys the illumination light of an illumination light source from a light entry connection to the distal exit end, is improved in accordance with the present invention in such a manner that fabrication and assembly of the endoscope, and in particular the light guide, is greatly simplified.

Furthermore, in accordance with the present invention an effective mode of sterilizing the endoscope is also now possible, and thus is extremely important with regard to diseases such as AIDS.

The present invention is based on a point of connection between the actual endoscope and the image pick-up, not "behind the eyepiece" but rather, directly behind the image-carrying unit which may be composed of rod lenses in a known manner or of a bundle of fibers. The pick-up can be arranged directly in the proximal image plane of the image-carrying unit, and a lens, such as used in conventional TV cameras for endoscopy, can be eliminated, thereby reducing the elaborate construction, simplfying fabrication and simultaneously raising the transmission factor so that it is possible to work with weaker illumination light sources or obtain a lighter and sharper image with the same illumination strength.

Above all, in a presently preferred embodiment according to the present invention, the TV camera can be miniaturized substantially further than is the case with conventional endoscope cameras as the camera practically only consists of the image pickup.

This of the present invention endoscope has the additional advantage that coupling-in the illumination light is simplified. For this purpose, a light guide surrounds the image pick-up and is designed in such a manner that it is connected to the light guide of the endoscope when the TV camera is attached to the endoscope.

The above described construction obviates the lateral coupling-in sockets of conventional endoscopes, which sockets make fabrication more expensive and often result in irregular illumination of the image.

Nonetheless, with the endoscope of the present invention it is possible to still observe the endoscope image additionally or exclusively just visually.

For this purpose a, known eyepiece is attached to the body of the endoscope instead of the TV camera or, in addition to it, by way of an optical image divider. This eyepiece is usually designed in the same manner as the eyepieces in conventional endoscopes which are fixed to the image-carrying part. In particular, the eyepiece can be provided in a, known manner with a lateral coupling-in socket for the illumination light.

The TV endoscope of the present invention has, moreover, the advantage that sterlization of the individual elements is simplified as the actual endoscope is composed of fewer parts.

A feature of the present invention is that the light guide hollow cylinder made of a transparent and optically clear material surrounding the lens and the relay-lens system.

Another feature of the present invention is that the light of the illumination light source can be coupled into the circular front face of the hollow cylinder.

Thus, the present invention breaks with two seemingly irrefutable principles of construction of prior art endoscopes.

Instead of a large number of light-guide fibers, which are painstakingly laid into the round space between the relay-lens system and the outer protective tube of the endoscope and subsequently have to be arranged, a one-piece part is employed that serves as the light guide. The coupling-in of the illumination light into this part does not occur from the side via a light-guide socket, but rather via the circular front face of the light guide.

In this way, the time-consuming assembly steps of conventional endoscopes are eliminated. Of substantial importance is the fact that the endoscope body of the present invention has the advantage that the illumination light is conveyed over a substantially greater area than is the case with the prior art endoscopes. In particular, it must be taken into consideration that, even with the most painstaking assembly, some of the light-guide fibers are "dead" in the prior art endoscopes, i.e. no light is conveyed through these light-guide fibers to the distal end. If such dead of inactive light-guide fibers occur en masse in a certain angular range in such prior art endoscopes an irregular illumination of the object field results.

In the endoscope body of the present invention, the illumination light is evenly coupled-in via the entire circular front face so that an even or uniform illumination of the object field is obtained.

The one-piece light guide of the present invention can be made of any transparent, optically clear material, such as, for example an optical glass.

According to the present invention, the light-exit area of the image carrier surrounding the image pick-up is at a fixed distance in the direction of the longitudinal axis of the endoscope from the image pick-up arranged in the image plane of the image-carrying unit. This has the advantage that no scattered light from the point of connection of the two light guides can strike the image pick-up.

An additional lens element can be provided between the image-carrying unit and the image pickup. This additional lens element serves to adapt the size of the endoscope image to the dimensions of the image pick-up.

Furthermore, it is preferable if a camera connection cord is connected to the TV camera by a plug in which there is a space perpendicular to the longitudinal axis of the cord from the light-guide coupling and the connection elements. In this manner, the light guide is prevented from overheating the electrical connections and, under certain circumstances, the electric elements provided in the plug.

Overheating is also prevented by the arrangement of the electric connection lines which surround the light guide in the camera connection cord.

Another significant advantage of the present invention is that a separate light-guide cord is eliminated so that the endoscope, in contrast to conventional TV endoscopes, only has a single connection cord.

Another feature of the present invention is that the light guide is as a hollow cylinder composed of an optically clear plastic material. One such plastic material is polycarbonate which has an advantage that, among other things, it can easily be processed by injection diecasting so that the light guide can be easily and cost-efficiently fabricated as a diecast piece. It is also within the contemplation of the present invention, however, that the invented light guide can also be fabricated as yardage from respective tubes and, if needed, subsequently submitted to thermal treatment.

The light guide of the present invention, which has a hollow cylinder made of a transparent and optically clear material, can, in particular, become a cylindrical section with a larger inner and outer diameter in the proximal region. In this event, the free front face of the region with the greater diameter forms the light-entry area for the illumination light.

The above described embodiment has the advantage that the image transmission system, or the image representation system adjacent to the relay-lens system can have a larger diameter than the relay-lens system.

In any case, however, it is preferable that the front face of the light guide serving as the light-entry area lies in the longitudinal direction of the endoscope body before or behind the proximal image plane of the relay-lens system because reflections at the light-entry area do not enter the image plane.

The light guide utilized in accordance with the present invention has the additional advantage that it is possible in a simple manner to let the illumination light emerge at an angle which contains the optical axis of the oblique view objective with the longitudinal axis of the endoscope body by effectively bevelling the front face of the light guide serving as the light-exit area so that coaxiality between illumination and observation is warranted by a cost-efficient fabrication step. Nonetheless, the light guide of the present invention ensures uniform illumination of the object field.

A light-absorbing and/or reflecting elements for preventing the light from the light guide from passing into the relay-lens system and cause reflections is provided between the hollow cylinder forming the light guide and either the objective or the relay-lens system.

The above mentioned element may by way of illustration, be a plastic shrinking hose, into which the elements of the relay-lens system can be inserted in the proper position and which subsequently is shrunk by a thermal effect. In this manner, this element simultaneously also holds the elements of the relay-lens system so that a lens or objective barrel in the conventional sense is eliminated.

These elements may also be made of an optically clear plastic material, which for its part may, by way of illustration, be an injection diecast polycarbonate.

By virtue of the aforementioned improvements, the production costs of a conventional endoscope are reduced in such a manner that the endoscope can be utilized as a disposable endoscope. Presently comparable conventional endoscopes cost substantial monetary amounts which in itself prohibits utilizing them as disposable endoscopes.

Nonetheless, the endoscope of the present invention is provided with a plastic diecast piece, which has a flange element designed in a known manner for connection with the shanks of prior art endoscopes. The piece can be utilized at any time in the endoscope systems of the present invention instead of prior art endoscopes.

Working and observing, by way of illustration, with an eyepiece fixed to the endoscope body continues to be possible.

It has been found preferable that the endoscope body, contrary to prior art endoscopes, should not have an observing piece fixed to the body, but rather an eyepiece or a TV camera should be selectively attached to the endoscope body.

In applying the eyepiece, it is preferable if it has a known lateral light-line entry connection, which is connected, for example, via glass fibers to a circular illumination light-exit area arranged facing the circular illumination light-entry area of the endoscope body. Despite this design in which the eye-piece is constructed substantially similar to those in prior art endoscopes with fixed eyepieces, there are substantial cost savings compared to conventional endoscopes due to the separation of the eyepiece and the endoscope body which permits one eyepiece on a number of endoscope bodies.

Furthermore, the TV camera may be designed such that a circular illumination-exit area surrounding the image pick-up faces the circular illumination light-entry area of the endoscope body.

Due to its cost-efficient production, the endoscope is of the present invention is not only suited as a disposable endoscope, which is, for example, gamma-sterilized prior to use, but it can also be sterilized with microwave irradiation due to its almost total fabrication of plastic material. In this event, it is preferable if the part to be sterilized is arranged over an evaporation bowl containing, e.g., sterile water. The water evaporating due to the microwave irradiation initially precipitates onto the endoscope plastic material, which remains cold, and dissolves crystalline residues present there.

BRIEF DESCRIPTION OF THE DRAWINGS

The objects, features and advantages of the present invention are made more apparent by the following description of preferred embodiments with reference to the accompanying drawings wherein.

DESCRIPTION OF PRESENTLY PREFERRED EMBODIMENTS

Figure 1:
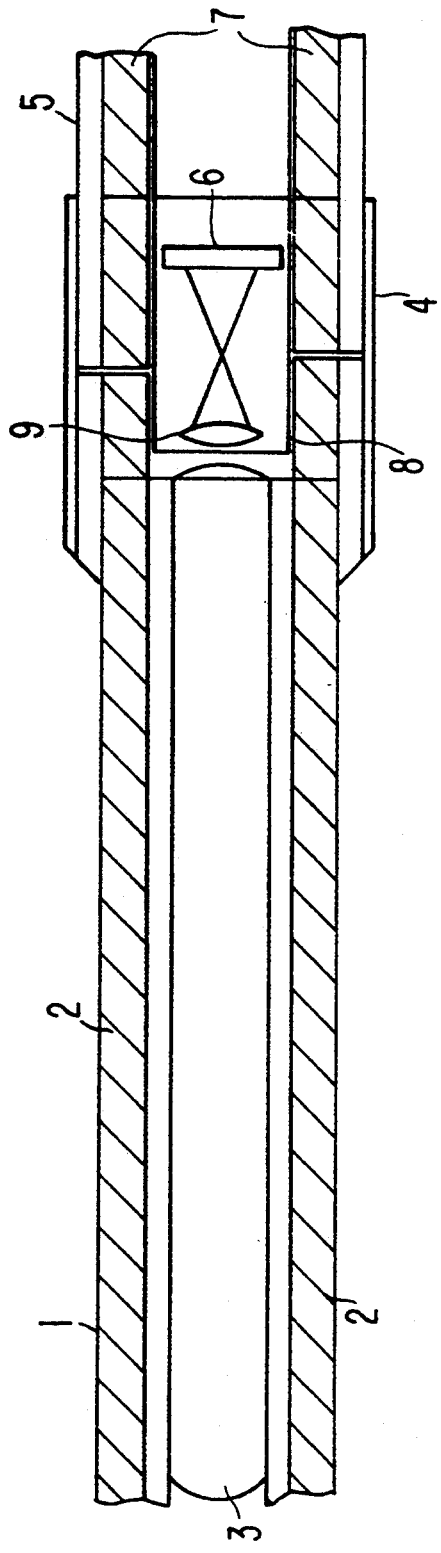
FIG. 1 is a cross-section, schematic view of an endoscope designed in accordance with the present invention having an image pick-up attached to it.

FIG. 1 shows a first preferred embodiment of an endoscope having a sleeve 1 of generally known construction, which may be made, by way of illustration, of stainless steel or also of a plastic material, and in which a light guide 2, an image-carrying unit 3 and a lens (now shown) at the distal end are provided.

Light guide 2 and the image-carrying unit 3 are generally known, and, by way of illustration, the image-guiding unit 3 is made of rod lens optics or a bundle of fibers.

At its proximal end, the endoscope has, in addition to a coupling of known design for connection to an endoscope shank, another coupling element 4, which in the illustrated preferred embodiment, is a clicker sleeve. A spring-loaded ball or a toroidal sealing ring is provided in the clicker sleeve for detention. By virtue of this coupling element 4, a TV camera 5 can be connected to the endoscope in such a manner that the light-sensitive area of a image pick-up 6 is in the proximal image plane 3' of image-carrying unit 3. Furthermore, the TV camera 5 has a light-guiding element 7, which encompasses the image pick-up 6 and serves to couple-in the illumination light in the light guide 2 of the endoscope.

The point of connection between light-carrying element 7 and the light guide 2 is at a fixed distance in the axial direction of the endoscope from the image pick-up 6. In the illustrated embodiment, it is closer the image-carrying unit 3 so that the image pick-up 6 is shielded by a sleeve 8 from scattered light which may occur at this point of connection. Furthermore, a lens 9 is provided, to adapt the size of the proximal image to the dimensions of the light-sensitive area of image pick-up 6.

Figure 2:
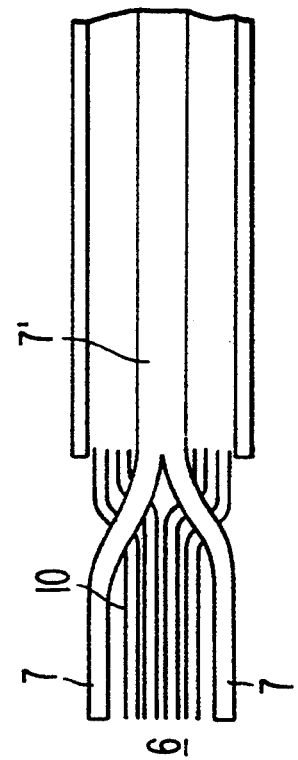
FIG. 2 is an isolated view of the course of the connection cord in the TV camera, or path

FIG. 2 shows the design of the connection cord in the TV camera.

In the region of image pick-up 6, the electric connection wires 10 are located inside and are surrounded by the light guide 7. After a short stretch, the circular, or hollow-cylindrical light guide 7 merges into hollow a cylindrical light guide 7', of which electric connection wires 10 then run to the outside of the light guide 7'.

Figure 3:
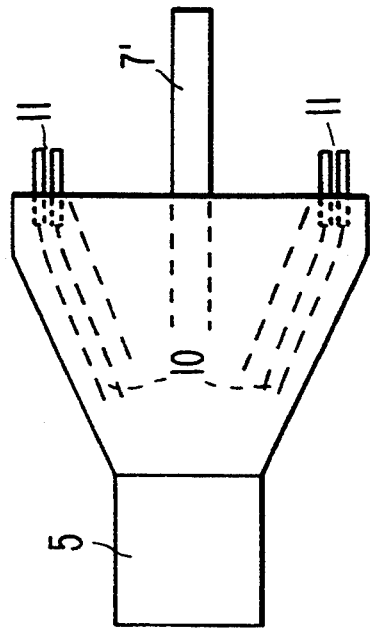
FIG. 3 is an isolated view of the connecting plug.

FIG. 3 shows a connecting plug between the TV camera 5 and a connection cord, which is not shown in detail. Electric connection wires 10 are at a greater distance from the light guide 7' in the plug than, by way of illustration, in the camera 5. In this way, electric contact elements 11 cannot get too hot, and therefore no contact problems can occur.

The endoscope of the present invention not only permits video observation of the endoscope image, but also permits detachment of the TV camera 5 and also allows attachment of an eyepiece for solely direct visual observation. This eyepiece may be of a known design, and may, in particular, be provided with a lateral connection socket for coupling-in the illumination light.

Moreover, a beam divider, which performs an optical intermediate-imaging, may also be mounted on the endoscope so that visual observation and pick-up of a video image are possible simultaneously.

The present invention has a particular advantage that there are distinctly fewer glass areas before the image pick-up than with conventional endoscopes so that the degree of transmission is greater and thus the video image lighter and sharper.

Furthermore, the cost of an endoscope set, i.e. for endoscopes with varying angle of view and/or direction of field of view, is significantly reduced as only one eyepiece has to be acquired for all the endoscopes. Endoscopes constructed in accordance with the present invention consisting of only one lens, an image carrier and a light guide without lateral coupling-in are distinctly cheaper to fabricate than conventional endoscopes.

Finally, the ability to sterilize the endoscope inserted into the body is improved.

Figure 4:
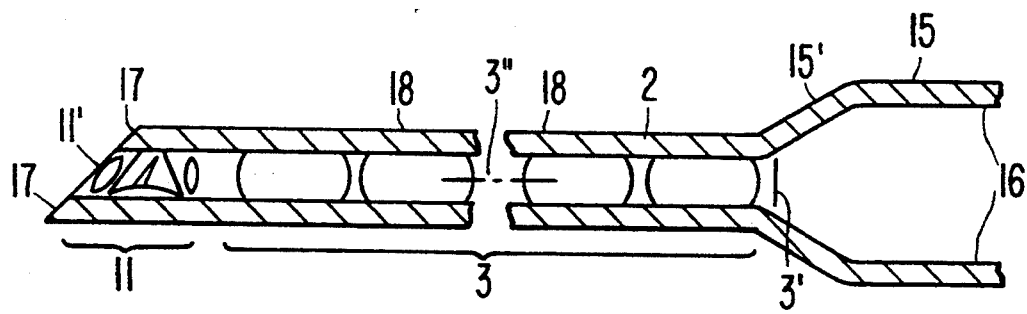
FIG. 4 is a cross-section view of an endoscope body designed in accordance with the present invention.

FIG. 4 shows another preferred embodiment of an endoscope in accordance with the present invention, which has a known objective 11. The image of the objective 11 is conveyed by an image-carrying system 3, consisting, for example, of a number of rod lenses and, if necessary, other lenses, from the distal end to a proximal image plane 3'. A light guide 2 surrounds the objective 11 as well as the relay-lens system 3.

Contrary to conventional endoscopes, the light guide 2 is made of a one-piece hollow cylinder, adjacent another cylindrical region 15 with a larger inner and outer diameter than that of the hollow cylinder light guide 2. The transition from cylinders 2 and 15 is continuous in the region 15' so that the light guide 2 can convey the light entering at the entry side of front face 16 of hollow cylinder 15 to the exit side (distal) front face 17. In the illustrated preferred embodiment, the objective is a so-called "oblique view objective", which is provided with prisms in addition to the lenses, so that the observation axis 11' of the objective 11 contains an angle with an optical axis 3" of the relay-lens system 3 and thereby with the longitudinal axis of the illustrated endoscope body.

In order to prevent the light from the light guide 2 from passing into the region of the relay-lens system or into the region of the objective 11 and causing reflections or overexposures, a light-impervious 18 is inserted between relay-lens system 3, respectively objective 11 and the light guide 2. This member 18 is, in the illustrated preferred embodiment, a plastic shrink hose. Into this plastic shrink hose are inserted first the relay-lens system lenses 3 and, if necessary, the lenses and prisms of the objective 11 which are then correctly positioned. Subsequently the shrink hose 18 is shrunk by the application of heat so that the lenses are contained without requiring a conventional lens barrel.

In the illustrated embodiment, the light guide 2 and, if necessary, the lenses of the objective 11 and the relay system 3 are made of a plastic material, such as polycarbonate, which is thermally pliable and can be injection diecast.

Thus, the light guide 2 can be fabricated, by way of illustration, from "yardage", with part 15 having a larger diameter due to respective thermal shaping, such as expansion.

The fabrication of lenses by injection-diecasting is substantially cheaper than the conventional production of glass lenses so that the manufacturing costs of the endoscope body of the present invention is distinctly reduced compared to prior art endoscopes.

An eyepiece or a miniature TV camera, as described in the preferred embodiment illustrated in FIG. 1, can be inserted into hollow cylinder 15.

In the shown preferred embodiment of FIG. 4, a light-impervious lacquer, such as, a polyurethane lacquer diluted with the respective color pigments, which, among other things, has the advantage that it is relatively compatible to tissue, is applied to the outside of the light guide. Furthermore, a plastic diecast piece with a flange element designed in a known manner for insertion in conventional endoscope shanks can be attached to the endoscope body.

Naturally, the endoscope body of the present invention may also be placed in a protective metal tube.

Figure 5:
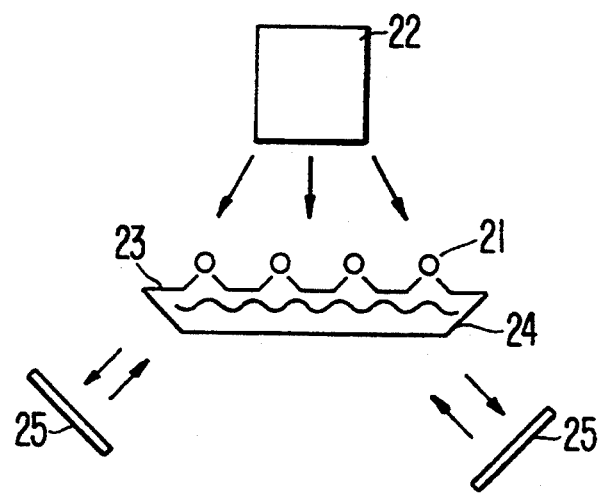
FIG. 5 is a schematic view of a sterilization device.

FIG. 5 shows a device for sterilizing the endoscope body embodiments illustrated in FIG. 1 and FIG. 4. An element of the present invention is, namely, that it was understood that, in particular, the endoscope body shown in FIG. 4 is excellently suited for microwave sterilization due to being entirely made of a plastic material. In order to do this, one or several endoscopes 21 are arranged in the microwave field of a microwave source 22, for example, on a grid 23. Grid 23 is preferably arranged on an evaporation bowl 14 with sterile fluid, by way of e.g. water, which is evaporated by the microwaves and removes dried and crystallized infective agents on the endoscope.

Furthermore, reflectors 25 are provided, which reflect the radiation so that endoscopes 21 are irradiated from all sides. The reflectors are arranged in such a manner that they do not reflect the radiation back into microwave source 22 so that it is not destroyed.

In accordance with the present invention it is to be further understood that the endoscope can be sterilized with microwaves even if a protective metal tube is employed as long as only one specific relationship between the diameter of the tube and the distance from the microwave source is maintained at a specific frequency.

Although the invention has been described and illustrated in detail, it is to be clearly understood that the same is by way of illustration and example, and is not to be taken by way of limitation. The spirit and scope of the present invention are to be limited only by the terms of the appended claims.

What is claimed is:

1. A reusable endoscope, comprising a body having one end constituting a proximal end and having an endoscope objective at another end thereof constituting a distal end, an image-carrying means having a relay lens system for conveying an image of the objective to a proximal end of the body, a light source provided by one of a separable single lens eyepiece and a separable television camera having a circular illumination exit area surrounding an image pickup thereof, and a light guide which conveys light from the light source to said distal end and which encompasses said image-carrying means, wherein said light guide is a hollow cylinder with a circular front face made of a transparent and optically clear material which surrounds said objective and the relay-lens system, and the light from said light source is transmitted into the circular front face of said hollow cylinder, and at least one of a light-absorbing element and reflecting element is operatively arranged between said hollow cylinder and at least one of said objective and said relay-lens system, wherein at least a portion of said endoscope body between said distal end and said proximal end is configured to be inserted into a human body and is made from a material which permits microwave sterilization and reuse.

2. An endoscope according to claim 1, wherein said hollow cylinder also includes a cylindrical section having an inner and outer diameter in a region of the proximal end which is larger than in a region of the distal end, and the circular front face between the inner and outer diameter of said cylindrical section constituting said light-entry area.

3. An endoscope according to claim 1, wherein a distal end of the light guide has a bevelled exit area constituting an observation direction of said objective.

4. An endoscope according to claim 1, wherein a shrinkable plastic hose is arranged between said hollow cylinder and said objective, and said relay-lens system comprises components held within said hose.

5. An endoscope according to claim 1, wherein light transmitting components of said relay-lens system are optically clear plastic material.

6. An endoscope according to claim 1, wherein said plastic material is polycarbonate.

7. An endoscope according to claim 1, wherein shanks are provided at the endoscope body and a plastic diecast piece having a flange element is configured to be inserted into the shanks.

* * * * *